(12) United States Patent
Mantas et al.

(10) Patent No.: US 6,833,005 B1
(45) Date of Patent: Dec. 21, 2004

(54) LIGAMENT GRAFT SYSTEM AND METHOD

(76) Inventors: John P. Mantas, deceased, late of Wellington, UT (US); by Noula L. Mantas, legal representative, 2262 Sego Lily Dr., Wellington, UT (US) 84542

( * ) Notice: Subject to any disclaimer, the term of this patent is extended or adjusted under 35 U.S.C. 154(b) by 401 days.

(21) Appl. No.: 10/062,932

(22) Filed: Jan. 30, 2002

Related U.S. Application Data
(60) Provisional application No. 60/266,257, filed on Feb. 2, 2001.

(51) Int. Cl.⁷ .......................... A61F 2/08; A61B 17/28
(52) U.S. Cl. .......................... 623/13.13; 623/13.14; 606/72; 606/232
(58) Field of Search .................. 606/72, 86, 232; 623/13.11, 13.12, 13.13, 13.14, 13.17, 13.2, 13.19

(56) References Cited

U.S. PATENT DOCUMENTS

| | | |
|---|---|---|
| 5,037,422 A | 8/1991 | Hayhurst et al. |
| 5,041,129 A | 8/1991 | Hayhurst et al. |
| 5,211,647 A | 5/1993 | Schmieding |
| 5,224,946 A | 7/1993 | Hayhurst et al. |
| 5,236,445 A | 8/1993 | Hayhurst et al. |
| 5,268,001 A | 12/1993 | Nicholson et al. |
| 5,300,077 A | 4/1994 | Howell |
| 5,306,301 A | 4/1994 | Graf et al. |
| 5,380,334 A | 1/1995 | Torrie et al. |
| 5,425,733 A | 6/1995 | Schmieding |
| 5,456,685 A | 10/1995 | Huebner |
| 5,603,716 A | 2/1997 | Morgan et al. |
| 5,643,220 A | 7/1997 | Cosme |
| 5,643,266 A | 7/1997 | Li |
| 5,643,273 A | 7/1997 | Clark |
| 5,645,588 A | 7/1997 | Graf et al. |
| 5,674,224 A | 10/1997 | Howell et al. |
| 5,707,395 A | 1/1998 | Li |
| 5,769,894 A | 6/1998 | Ferragamo |
| 5,785,714 A | 7/1998 | Morgan et al. |
| 5,814,071 A | 9/1998 | McDevitt et al. |
| 5,871,504 A | 2/1999 | Eaton et al. |
| 5,891,150 A | 4/1999 | Chan |
| 5,906,632 A | 5/1999 | Bolton |
| 5,918,604 A | 7/1999 | Whelan |
| 5,919,196 A | 7/1999 | Bobic et al. |
| 5,931,840 A | 8/1999 | Goble et al. |
| 5,931,869 A | 8/1999 | Boucher et al. |
| 5,993,459 A | 11/1999 | Larson et al. |
| 6,036,694 A | 3/2000 | Goble et al. |
| 6,045,554 A | 4/2000 | Grooms et al. |
| 6,056,752 A | 5/2000 | Roger |
| 6,099,530 A | 8/2000 | Simonian et al. |
| 6,221,107 B1 * | 4/2001 | Steiner et al. ........... 623/13.14 |

* cited by examiner

*Primary Examiner*—David O. Reip
*Assistant Examiner*—D. Jacob Davis
(74) *Attorney, Agent, or Firm*—Kelly Lowry & Kelley, LLP

(57) ABSTRACT

A ligament graft system and method are provided for securely anchoring a ligament graft to patient bone, principally for use with autogenous hamstring graft tendons utilized for ligament replacement such as reconstruction of the anterior cruciate ligament of the human knee. An elongated ligament graft is assembled between femoral and tibial fixation units, and the thus-assembled system is fitted into and through generally aligned tibial and femoral tunnels formed in patient bone. A pivotally mounted anchor pin at a leading end of the femoral fixation unit positionally shifts upon emergence from the femoral tunnel to overlie and seat securely upon cortical bone. A trailing or lower end of the tibial fixation unit is adapted to engage and seat against cortical bone, wherein the tibial fixation unit can be adjustably positioned to variably select the tension applied to the ligament graft.

21 Claims, 10 Drawing Sheets

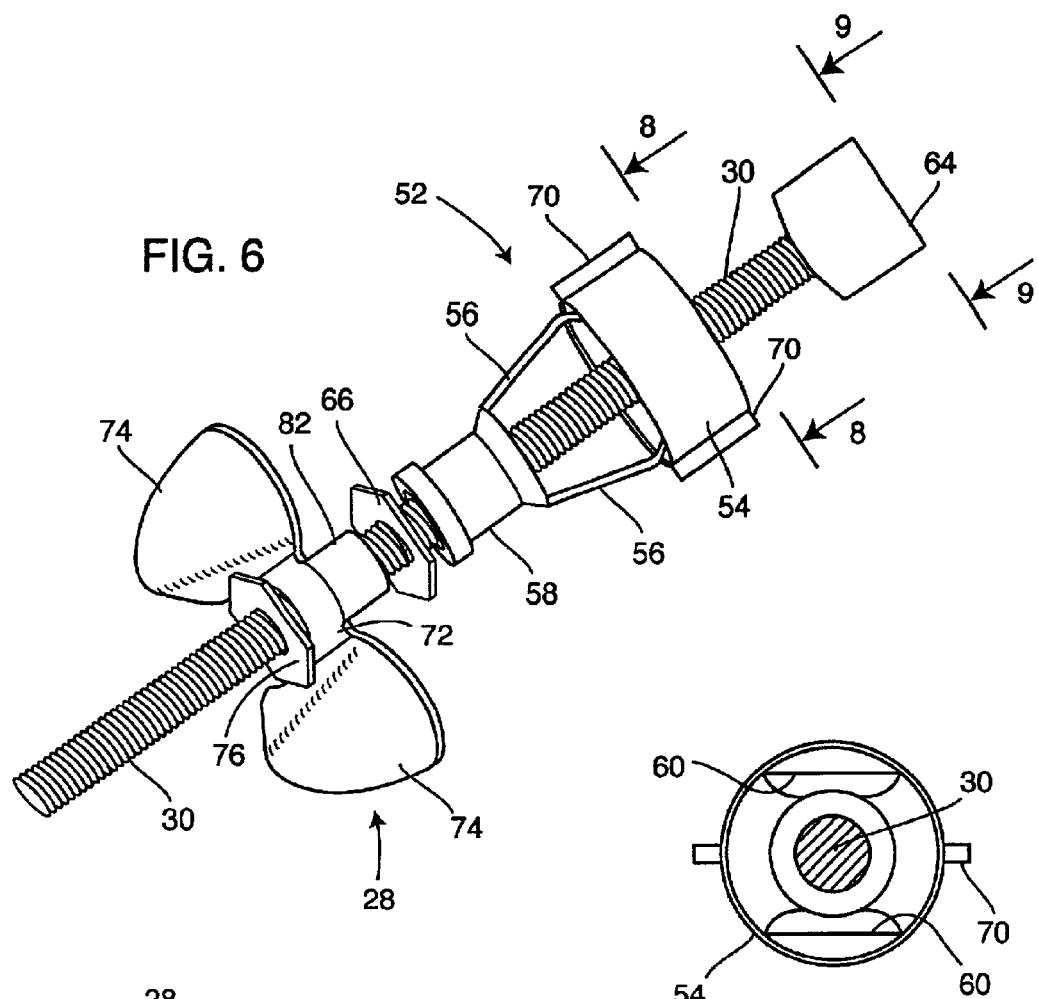
FIG. 6
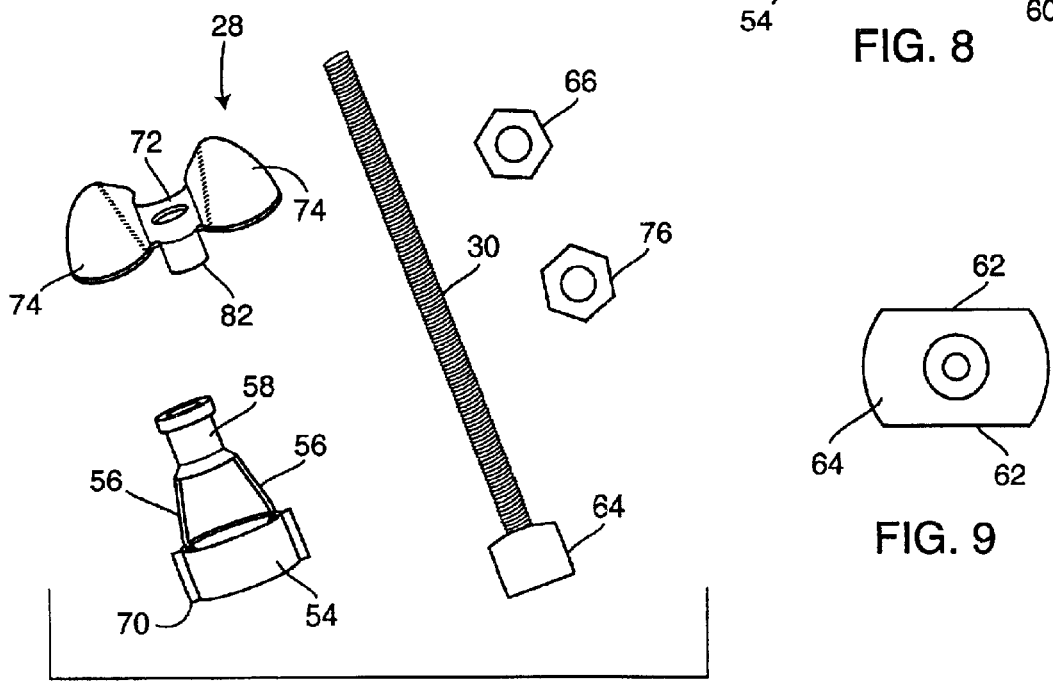
FIG. 8
FIG. 7
FIG. 9

FIG. 11
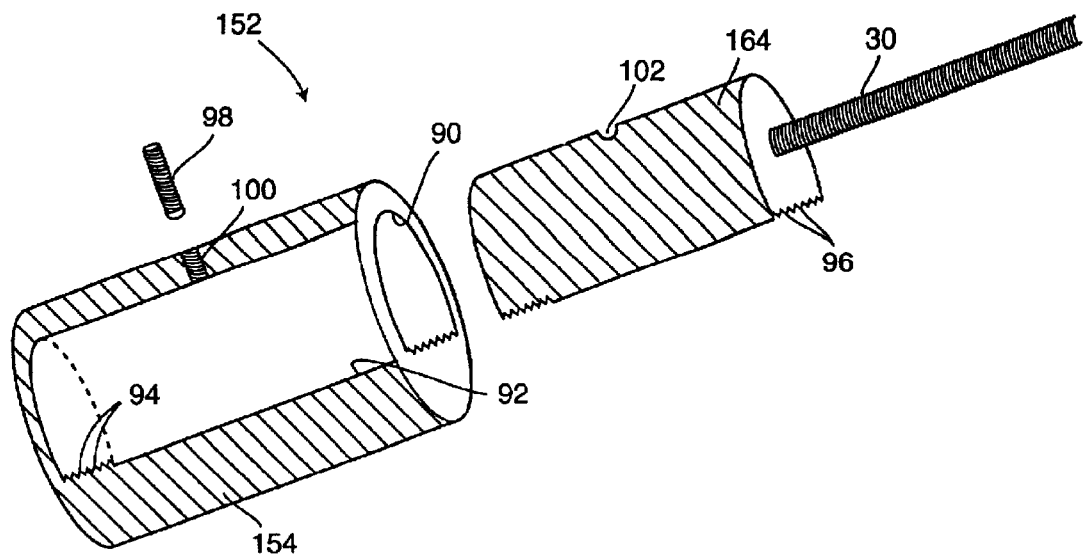
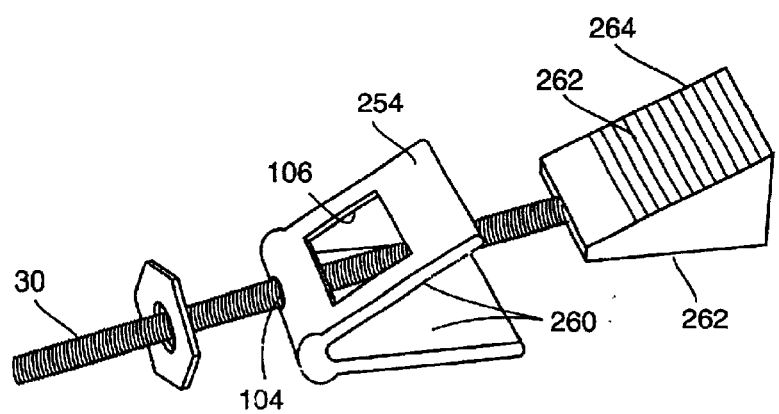
FIG. 12

LIGAMENT GRAFT SYSTEM AND METHOD

This application claims the benefit of copending Provisional Application No. 60/266,257, filed Feb. 2, 2001.

BACKGROUND OF THE INVENTION

This invention relates generally to improvements in devices and related installation procedures for surgical implantation of ligament grafts, such as a ligament graft used in the reconstruction of the anterior cruciate ligament of the human knee. The invention provides improved femoral and tibial fixation units attached to opposite ends of a ligament graft and adapted to seat firmly and securely against cortical bone. The invention further provides means for variably and selectively adjusting the tension applied to the implanted ligament graft.

Ligament grafts have been increasingly used in surgical reconstruction of human joints, particularly with respect to surgical knee reconstruction. As one common example, reconstruction of the anterior cruciate ligament may entail removal of a damaged natural ligament and replacement thereof by a ligament graft such as autogenous hamstring graft tendons harvested from the patient. In a typical procedure, a pair of generally aligned and relatively small tunnels are formed in the adjoining ends of the femoral and tibial bones at locations near the normal attachment sites of the natural anterior cruciate ligament. The ligament graft is positioned with its opposite ends extending into and/or through these femoral and tibial tunnels, and thereat fastened to the patient bone. A wide variety of different fastening structures and related methods have been proposed, such as the use of bone screws, bone staples, and the like, many of which involve anchoring of one or both ends of the ligament graft to relatively soft cancellous bone material. Other fastening devices and methods have looped the ends of the ligament graft through sutures which are in turn attached to patient bone.

Pre-existing systems and methods for anchoring the ligament graft have exhibited a number of disadvantages and potential failure modes. More specifically, anchoring of the ligament graft to relatively soft cancellous bone may permit the mounting structure to work loose over time, particularly when subjected to large physiologic loads associated with strenuous physical activity. The use of sutures to support one or both ends of the ligament graft provides a relatively unstable connection which can stretch or creep over time to provide a nonrigid fixation point. In addition, prior ligament graft attachment methods have not adequately restrained the ligament in a substantially centered position within the bone tunnels, without side-to-side sway motion or twisting, resulting in potential widening of the bone tunnels. Such tunnel widening abrades and wears the ligament graft and can result in undesirable loosening of the ligament graft. Additionally, conventionally available systems have not allowed equal distribution of force applied to the fibers of the ligament graft. Lastly, prior anchoring systems and methods have generally not provided a simple yet easily manipulated mechanism for variably and closely selecting the tension force applied to the implanted ligament graft.

The present invention provides an improved ligament graft placement and anchoring system which overcomes these problems and disadvantages by structurally supporting the ligament graft from relatively hard cortical bone, while additionally providing a simple and easily adjustable mechanism for variably selecting the tension force applied to the ligament graft, prior to completion of the surgery.

SUMMARY OF THE INVENTION

In accordance with the invention, a ligament graft system and method are provided for securely anchoring a ligament graft to patient bone, wherein the ligament graft is supported in a secure and stable manner from cortical bone, and further wherein means are provided for closely and variably selecting the tension applied to the ligament graft. The graft system and method are designed principally for use with autogenous hamstring graft tendons utilized for ligament replacement such as arthroscopic aided reconstruction of the anterior cruciate ligament of the human knee, although it will be recognized and understood that the invention can be expanded to applications with other types of grafts and other joint reconstruction procedures.

In general terms, an elongated ligament graft is assembled between femoral and tibial fixation units, and the thus-assembled system is fitted into and through generally aligned tibial and femoral tunnels formed in patient bone. A pivotally mounted anchor pin at a leading or upper end of the femoral fixation unit is adapted for positional shifting upon emergence from the femoral tunnel to overlie and seat securely upon cortical bone. In one preferred form, a winged washer at a trailing or lower end of the tibial fixation unit is adapted to engage and seat securely against cortical bone. A set nut or lock nut adjacent to the winged washer is positioned to retain the winged washer, and also to variably select the tension applied to the ligament graft.

More particularly, in one preferred form of the invention, the elongated ligament graft is looped through an open stirrup formed at the trailing end of an elongated stirrup rod comprising a portion of the femoral fixation unit. The anchor pin has a generally bullet-shaped configuration and is mounted pivotally at a leading end of the stirrup rod. The free ends of the ligament graft trail from the stirrup and are threaded and captured between a wedge-shaped bolt head seated within a capture cylinder comprising a portion of the tibial fixation unit. An elongated threaded tibial adjustment bolt projects downwardly in a trailing direction from the bolt head and carries the low profile winged washer and associated set nut.

These system components are assembled prior to patient placement and are slidably fitted into and through the generally aligned and preformed tibial and femoral tunnels formed in patient bone, with the bullet-shaped anchor pin pivoted to a position generally in-line with the stirrup rod. In the preferred form, at least one suture may be attached to the anchor pin and threaded through the tibial and femoral tunnels, wherein this suture may be accessed and used to assist in pulling the system components into the bone tunnels. Upon emergence of the anchor pin from the femoral tunnel, the anchor pin is pivotally shifted to overlie and seat securely upon cortical bone at the upper end of the femoral tunnel. The tibial fixation unit is then drawn downwardly to apply a selected tension to the ligament graft, and the winged washer and associated set nut are suitably advanced on the threaded adjustment bolt to bear against cortical bone at the lower end of the tibial tunnel. Set or lock nuts are provided on the adjustment bolt to retain the graft capture cylinder and the winged washer thereon in the desired set positions. In addition, the winged washer desirably includes an anti-backout tab which can be bent or deformed by the surgeon to engage the associated set nut in a manner locking the wing nut against back-out rotation.

In an alternative preferred form, a modified tibial fixation unit includes the elongated tibial adjustment bolt which projects downwardly from the bolt head and associated graft capture cylinder has a plurality of enlarged surface elements such as hemispherically shaped elements formed along the length thereof. The adjustment bolt is adapted to be engaged and drawn downwardly by means of a suitable tensioning tool to apply a selected tension to the ligament graft. In the desired tensioned position, a lock clip is fitted onto the adjustment bolt to engage a selected one of the enlarged surface elements, wherein this lock clip is sized and shaped for relatively low profile bearing and seating against cortical patient bone at the lower end of the tibial tunnel.

Other features and advantages of the invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is a further enlarged and somewhat schematic perspective view of the tibial fixation unit shown in FIG. 4;

FIG. 7 is an exploded and reduced-size perspective view showing the tibial fixation unit of FIGS. 4 and 6 in unassembled form;

FIG. 8 is an enlarged sectional view taken generally on the line 8—8 of FIG. 6;

FIG. 9 is an enlarged sectional view taken generally on the line 9—9 of FIG. 6;

FIG. 11 is an enlarged and exploded perspective view illustrating one alternative preferred form of a graft capture means forming a portion of the tibial fixation unit;

FIG. 12 is an enlarged perspective view illustrating another alternative preferred form of a graft capture means forming a portion of the tibial fixation unit;

DETAILED DESCRIPTION OF THE PREFERRED EMBODIMENTS

Figure 1:
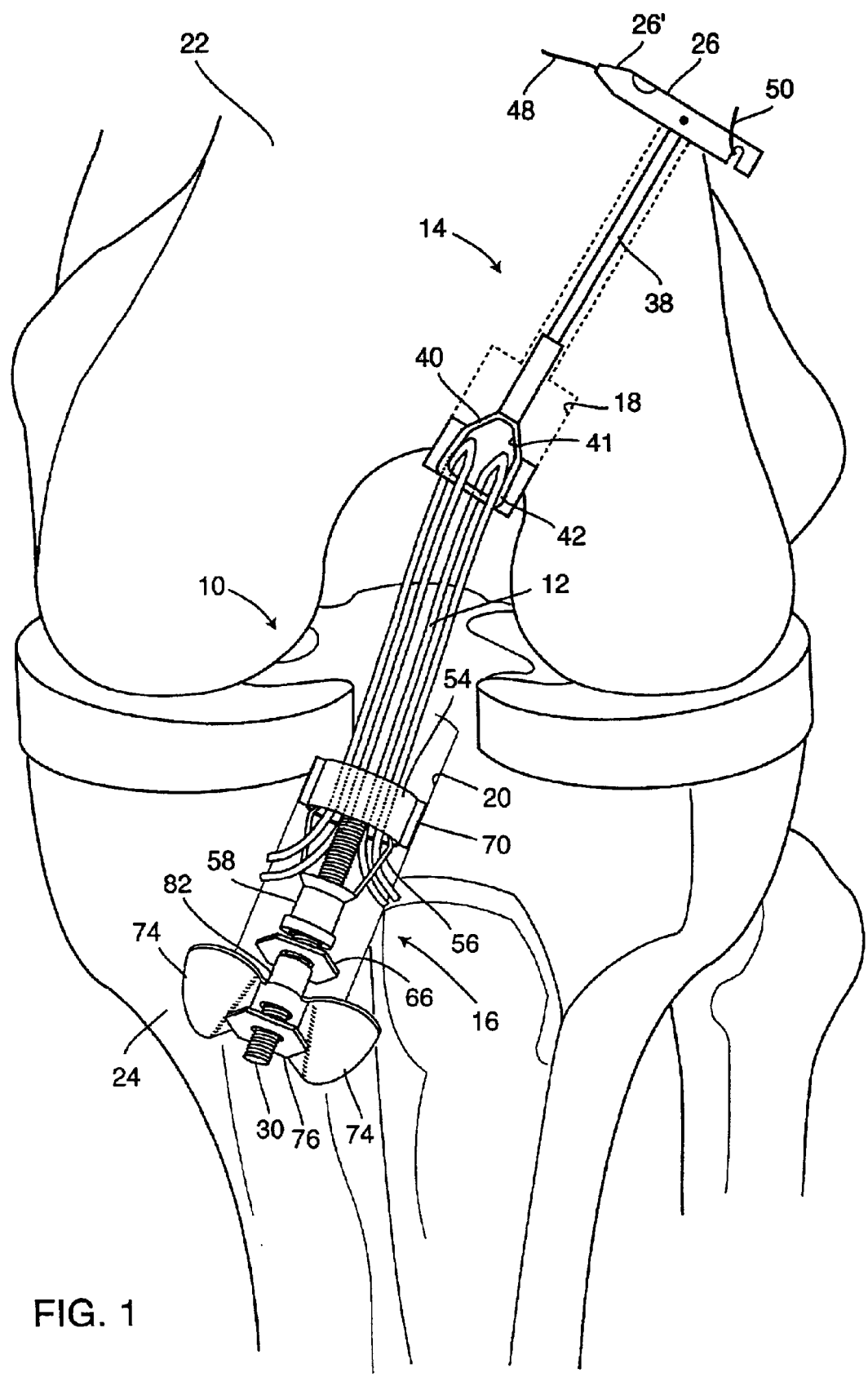
FIG. 1 is a front view of an exemplary human knee illustrating the ligament graft system and method in accordance with one preferred form of the present invention.

As shown in the exemplary drawings, an improved ligament graft system referred to generally in FIG. 1 by the reference numeral 10, and implantation method, are provided for securely anchoring a ligament graft 12 to patient bone. The ligament graft system 10 supports the ligament graft 12 in a secure and stable manner from relatively hard cortical bone surfaces, and further provides means for closely and variably selecting the tension force applied to the implanted ligament graft. The invention is designed primarily for use in arthroscopic aided reconstruction of the anterior cruciate ligament of the human knee, although persons skilled in the art will recognize and appreciate that the invention may be applied to alternative joint reconstruction procedures.

Figure 3:
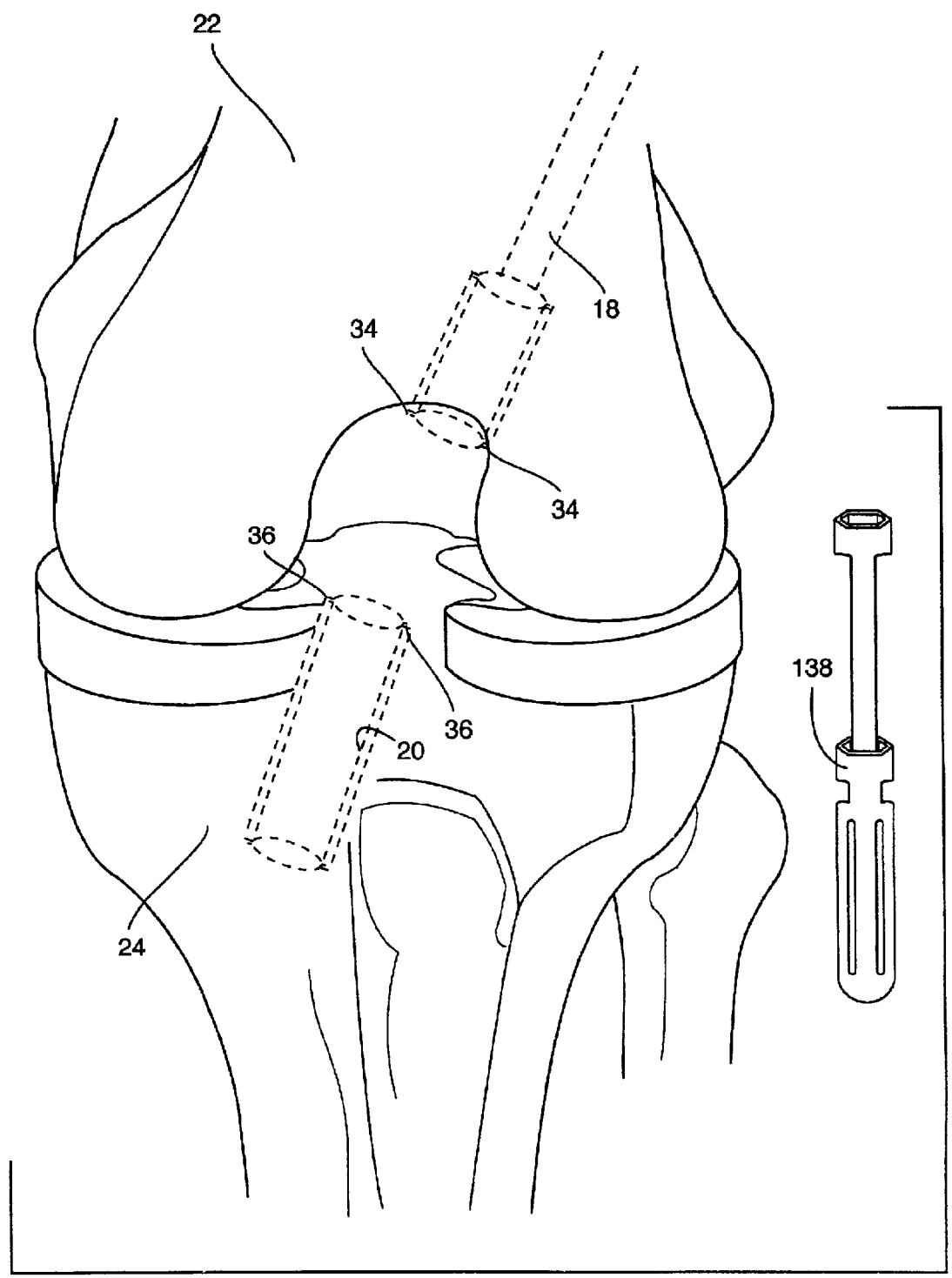
FIG. 3 is a front view of the human knee, similar to FIGS. 1 and 2, but showing the formation of generally aligned femoral and tibial tunnels in patient bone for subsequent placement of the ligament graft system in the reconstruction of the anterior cruciate ligament.
Figure 10:
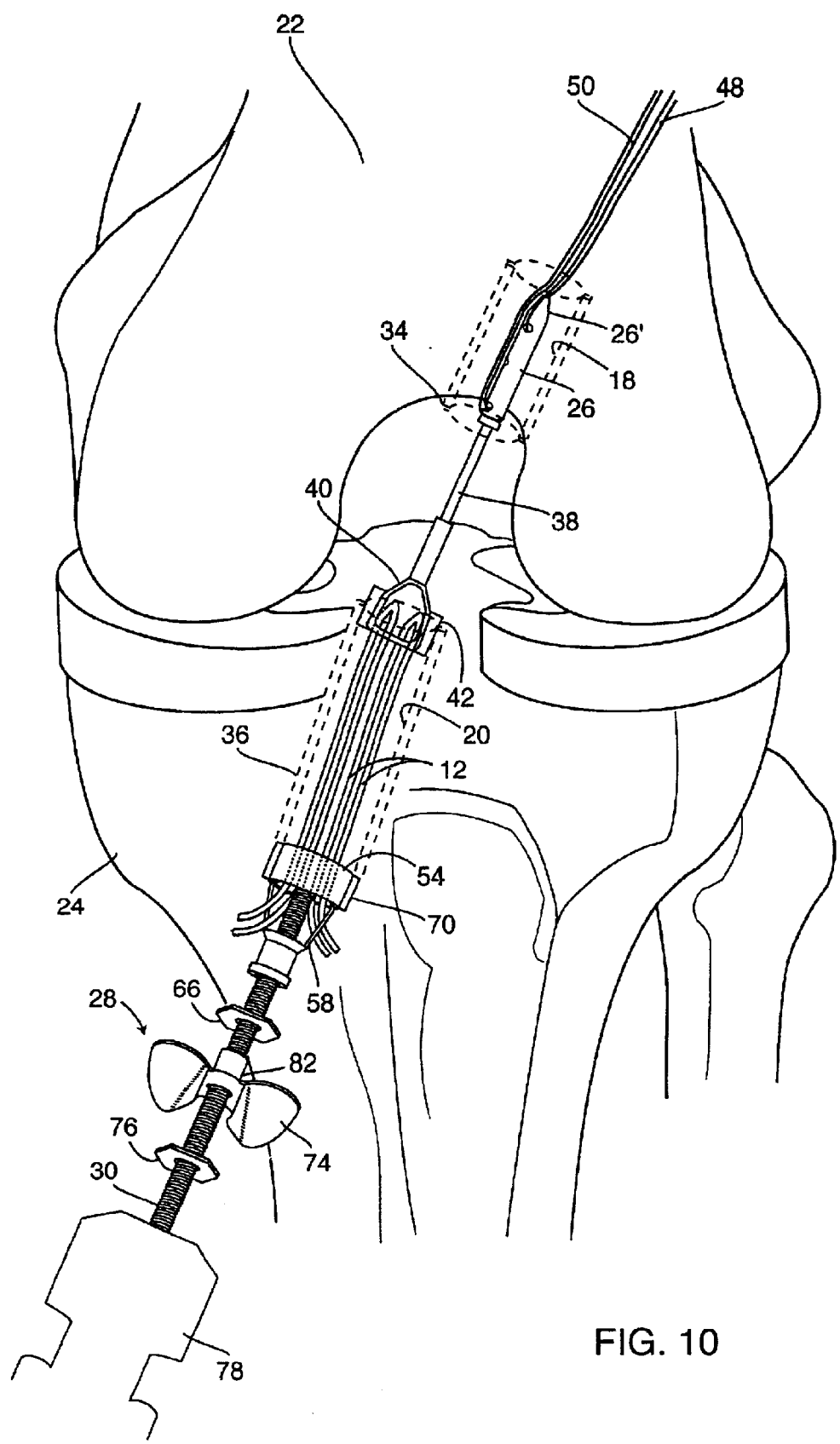
FIG. 10 is a front knee view similar to FIGS. 1 and 3, and showing placement of the ligament graft system into and through the femoral and tibial tunnels formed in patient bone.
Figure 13:
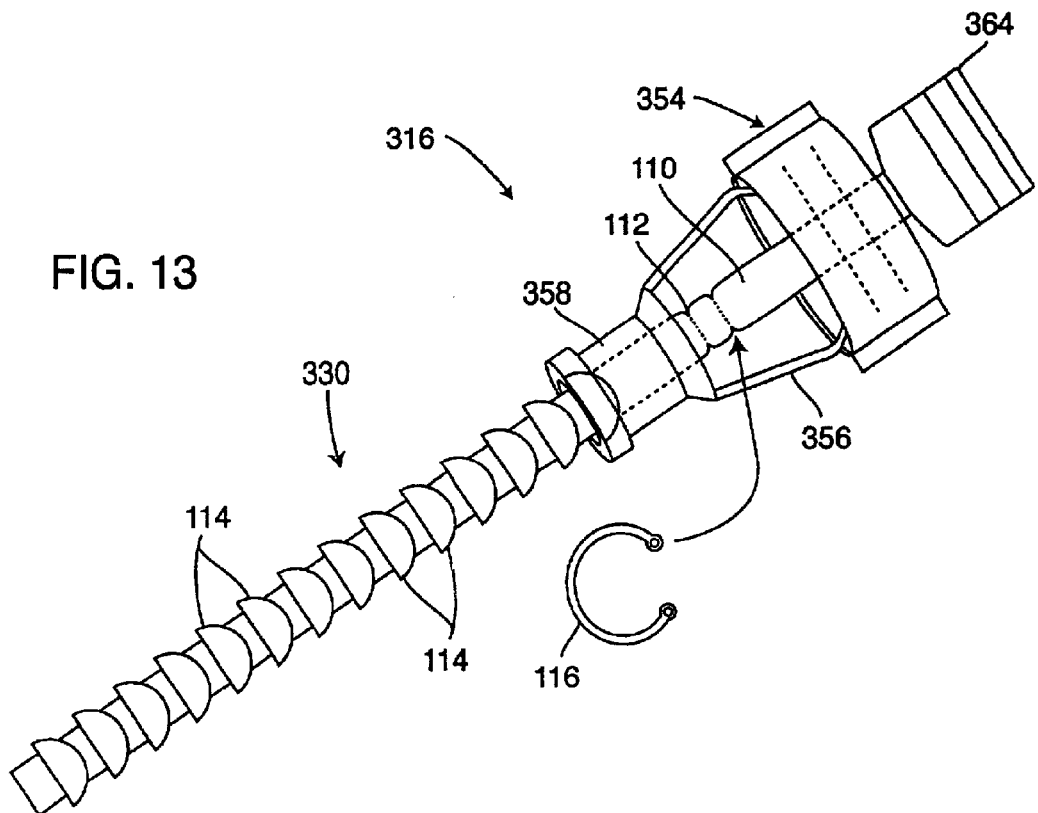
FIG. 13 is an enlarged, partially exploded and somewhat schematic perspective view showing a tibial fixation unit in accordance with an alternative preferred form of the invention.
Figure 14:
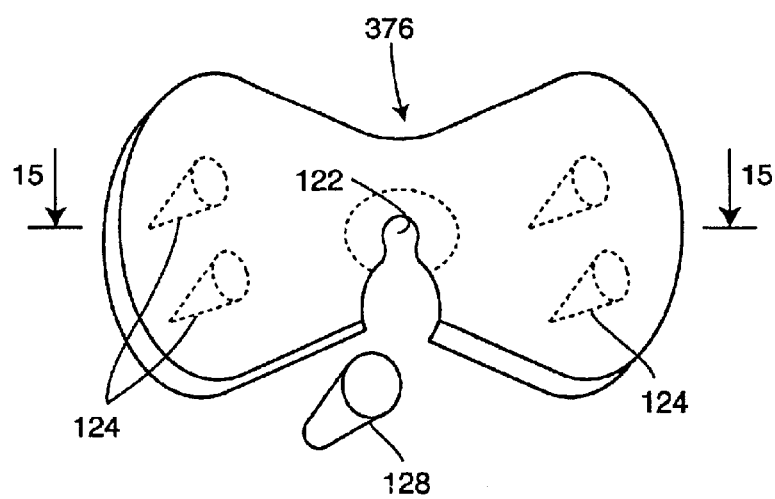
FIG. 14 is a perspective view of a lock clip for use with the tibial fixation unit of FIG. 13.
Figure 15:
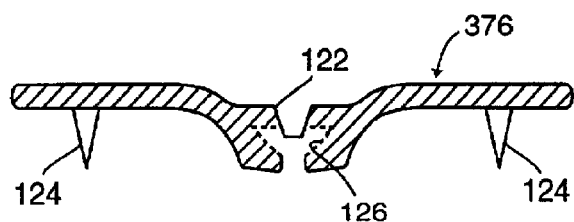
FIG. 15 is a sectional view taken generally on the line 15—15 of FIG. 14.
Figure 16:
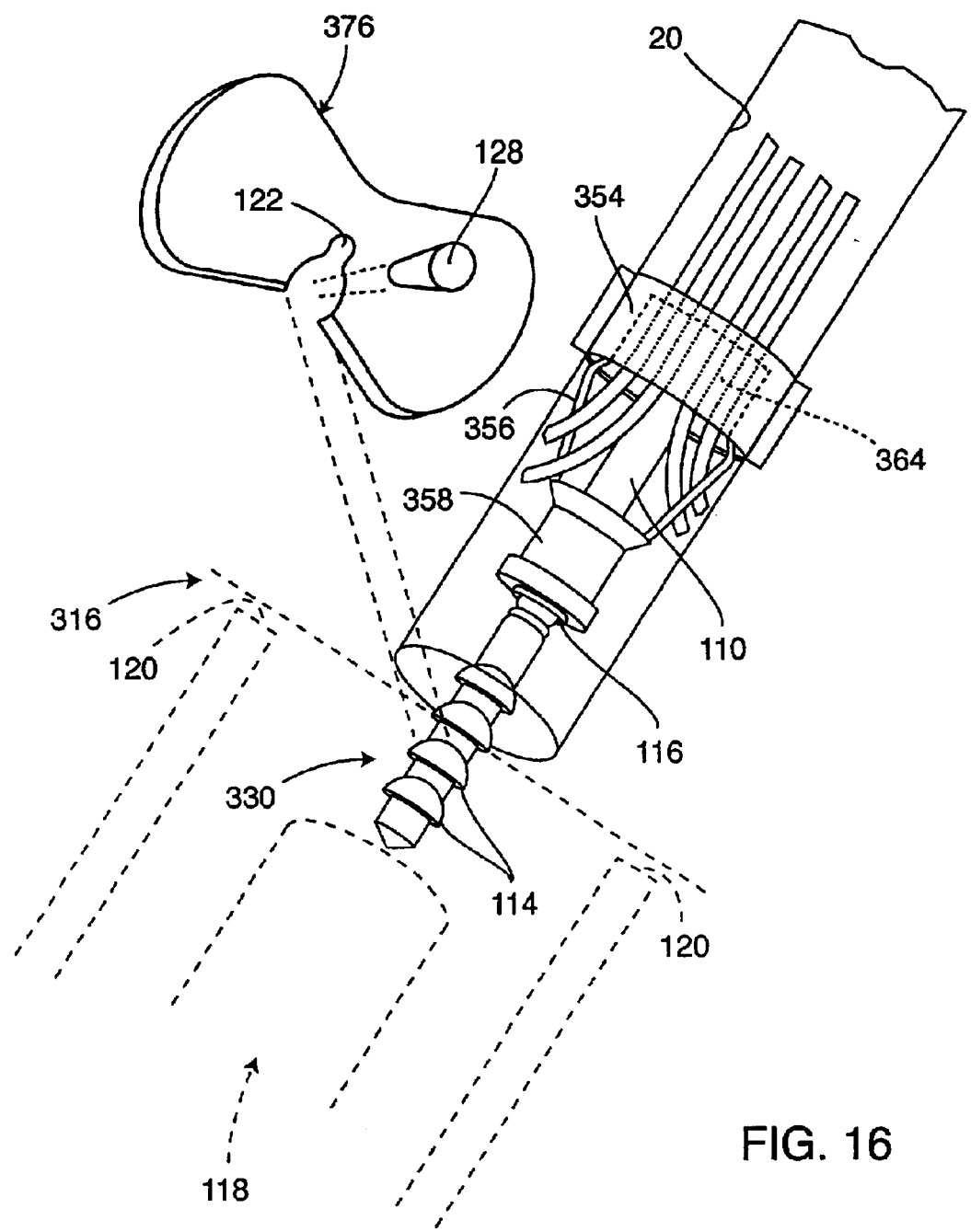
FIG. 16 is an enlarged, partially exploded and somewhat schematic view depicting installation of the tibial fixation unit of FIGS. 13–15 within a tibial tunnel formed in patient bone.

In general terms, and with reference to reconstruction of the anterior cruciate ligament as shown in the illustrative drawings, the ligament graft system 10 comprises an upper femoral fixation unit 14 and a lower tibial fixation unit 16 having the ligament graft 12 supported and suspended therebetween. The femoral and tibial fixation units of the graft system 10 are pre-assembled with the ligament graft 12, and the resultant assembled components are slide-fitted into and partially through pre-formed and generally aligned bone tunnels 18 and 20 formed in the adjoining ends of the patient's femur 22 and tibia 24, respectively (FIGS. 1, 3 and 10). An upper or leading end of the femoral fixation unit 14 includes a pivotally mounted anchor pin 26 adapted to overlie and bear against the relatively hard cortical bone surrounding the upper end of the femoral bone tunnel 18. A lower or trailing end of the tibial fixation unit 16, in accordance with one preferred form of the invention, includes a winged washer 28 that is carried on an elongated threaded adjustment bolt 30 and adapted to overlie and bear against the relatively hard cortical bone surrounding the lower end of the tibial bone tunnel 20. Importantly, a trailing set or lock nut 76 is rotatably adjustable on the bolt 30 for selectively setting and locking the position of the winged washer 28 in a manner applying a closely controllable tension force to the ligament graft 12.

Figure 2:
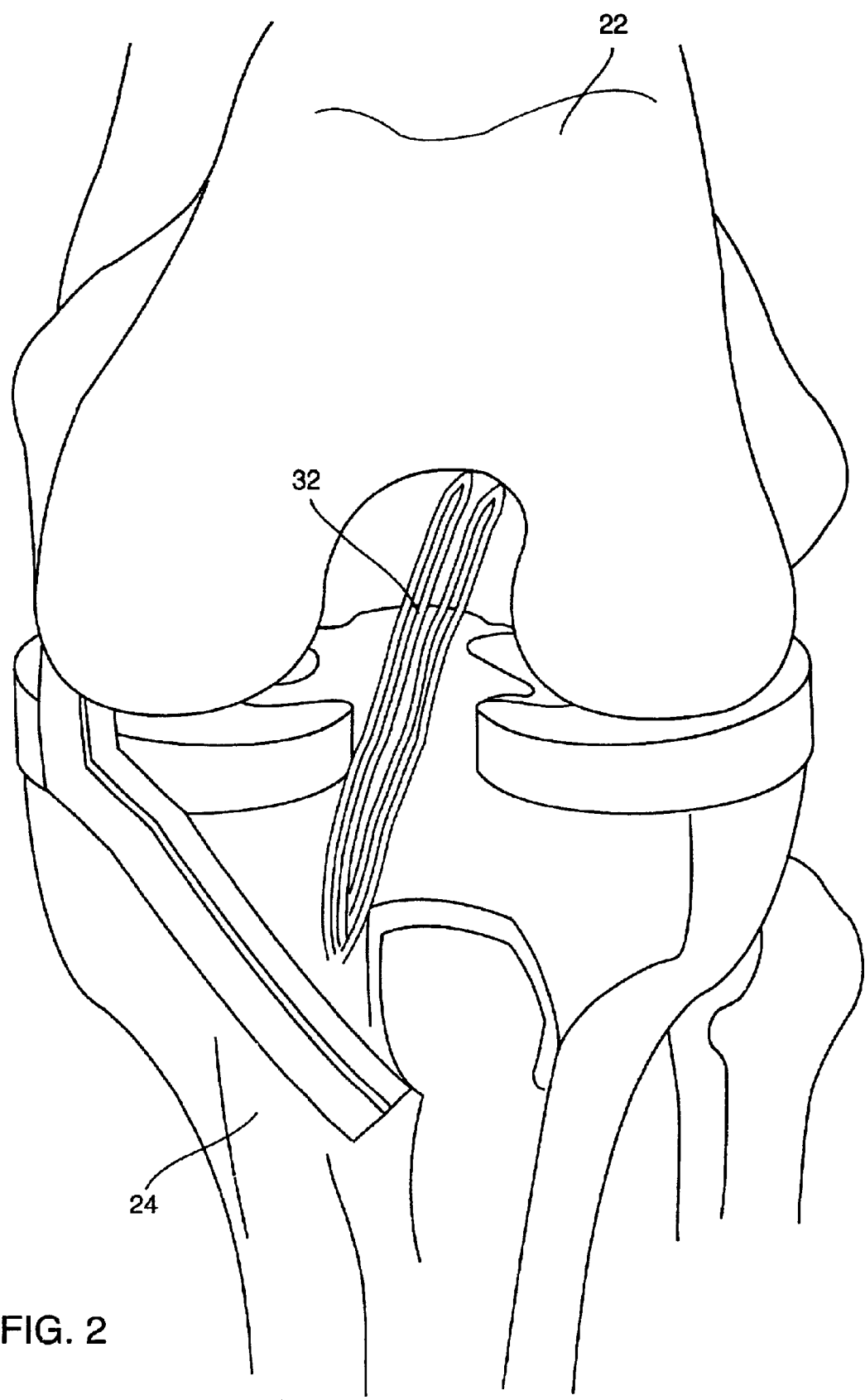
FIG. 2 is a front view of the human knee, similar to FIG. 1, but depicting the autogenous hamstring graft tendons for harvest and use in the ligament graft system and method of the present invention.

Use of the ligament graft system and related implantation method of the present invention typically follows a diagnosis of a tear in the anterior cruciate ligament 32, as shown in FIG. 2. In such event, a suitable ligament graft 12 is obtained for use in replacing the anterior cruciate ligament 32. FIG. 2 illustrates an exemplary and preferred ligament graft in the form of an autogenous hamstring graft. More particularly, FIG. 2 shows the gracilis and semitendinosus tendons of the left knee, wherein these tendons may be harvested for use as the ligament graft 12 using established techniques and commercially available tendon strippers (not shown). These tendons are cleared of any remaining muscle fibers and tubularized on the end cleared free of muscles fibers by using absorbable sutures.

FIG. 3 illustrates preparation of the knee for implantation of the ligament graft 12. As shown, the femoral and tibial tunnels 18 and 20 are formed in the adjoining ends of the patient's femur 22 and tibia 24, at generally aligned and angularly oriented positions corresponding generally with the directional axis of the natural anterior cruciate ligament 32 which is removed. These bone tunnels 18, 20 are formed using conventional available systems that allow for accurate tunnel placement and tunnel length. As shown, the femoral tunnel 18 comprises a relatively smaller diameter upper or leading end segment having an upper end emerging through the cortical bone surface, and a lower or trailing end merging with a comparatively larger diameter segment. The lower, larger diameter segment of the femoral tunnel 18 as well as the tibial tunnel 20 are additionally shaped to include a diametrically opposed pair of relatively shallow and longitudinally extending notches 34 and 36, respectively. These notches, which can be formed using a specially designed cannulated notching tool 138 as viewed schematically in FIG. 3, provide relatively shallow parallel troughs for engaging components of the femoral and tibial fixation units 14, 16 as will be described in more detail.

Figure 4:
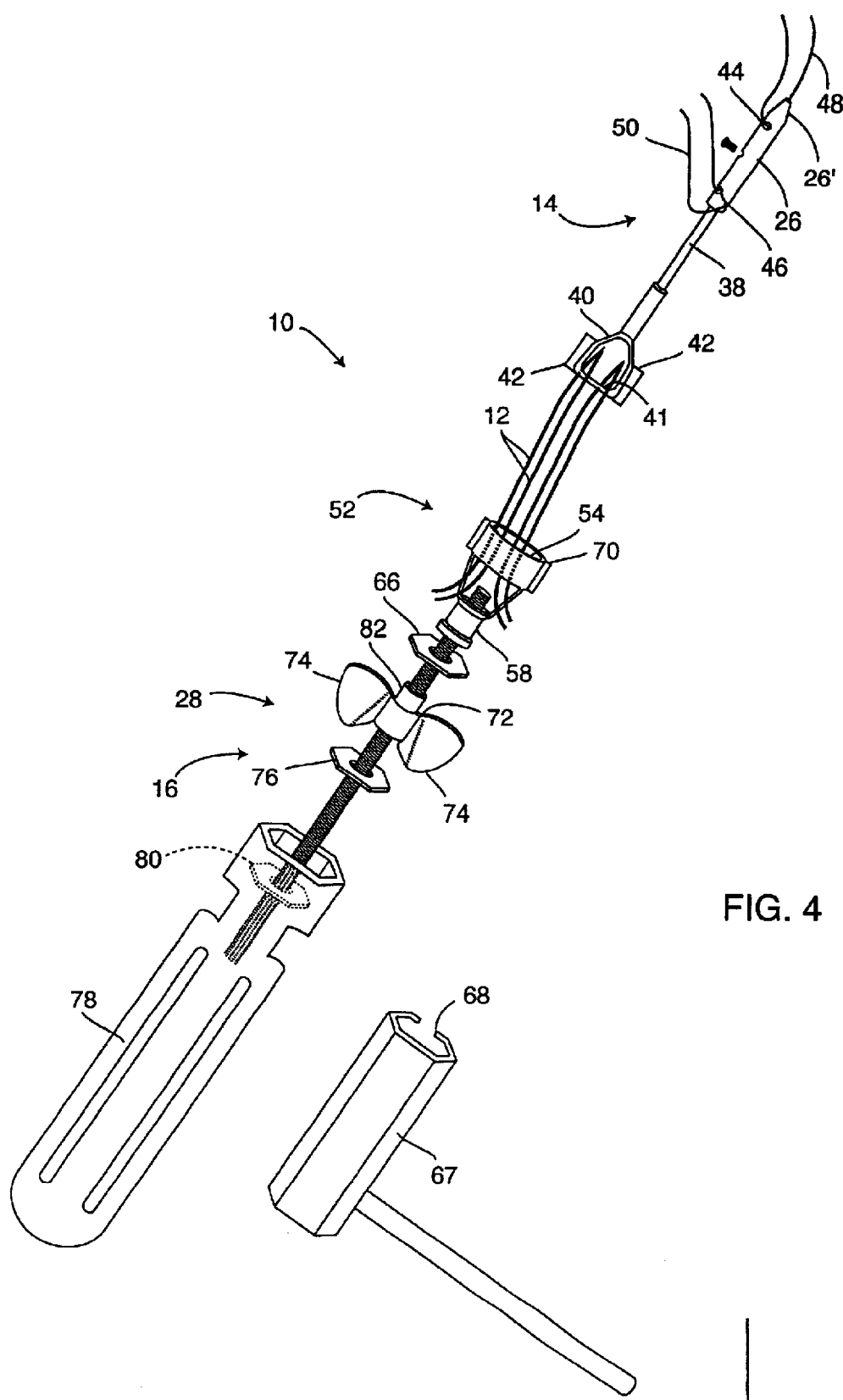
FIG. 4 is an enlarged perspective view showing femoral and tibial fixation units assembled with a ligament graft in accordance with the ligament graft system of the present invention.
Figure 5:
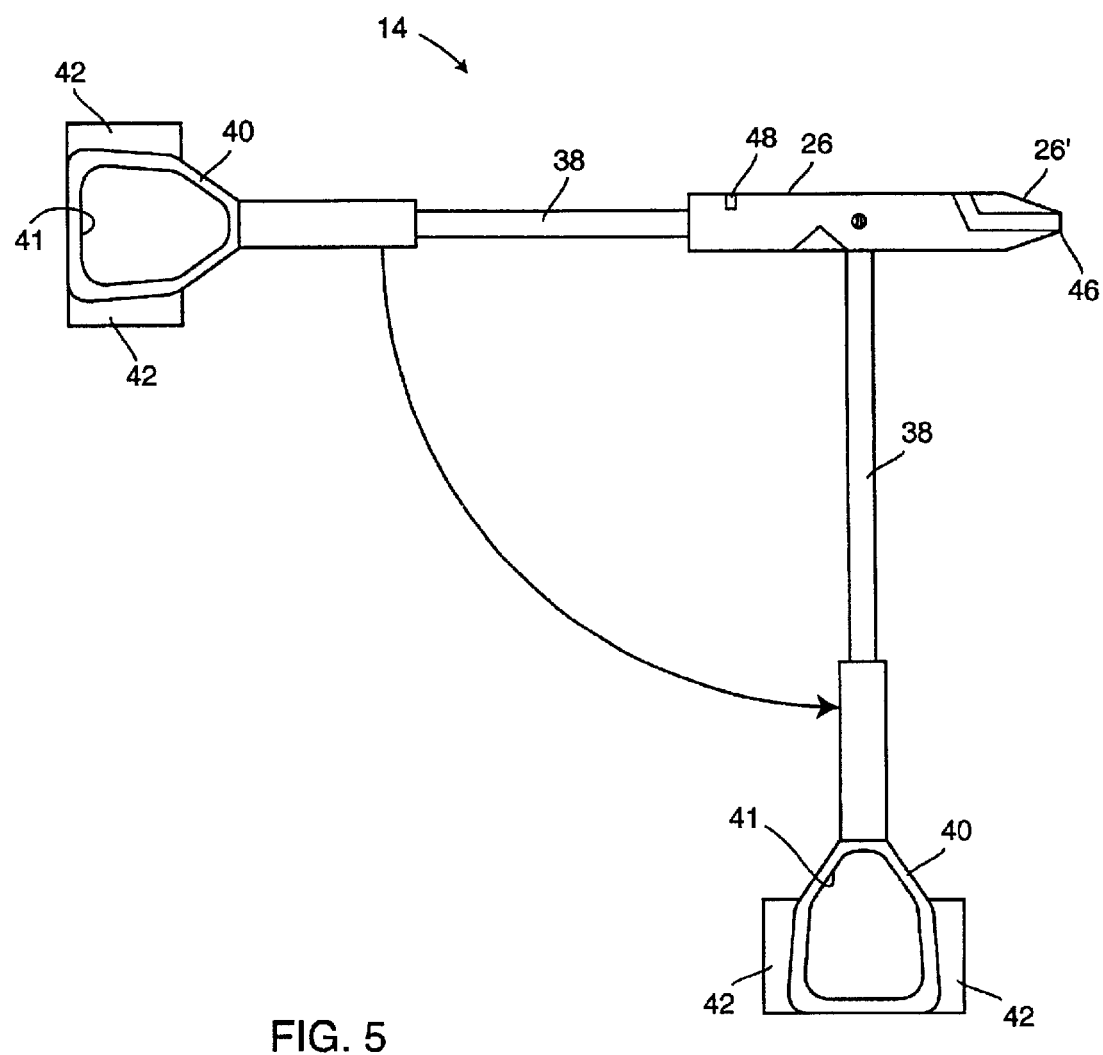
FIG. 5 is a further enlarged and somewhat schematic view of the femoral fixation unit shown in FIG. 4, and illustrating positional adjustment of a bullet-shaped anchor pin mounted pivotally at a leading end of an elongated stirrup rod.

The femoral and tibial fixation units 14, 16 are assembled with the ligament graft 12 prior to surgical placement into the patient's knee. More particularly, as shown in FIGS. 4–5, the femoral fixation unit 14 comprises an elongated femoral stem or stirrup rod 38 formed from a suitable surgical grade alloy or the like to include an enlarged and open-sided stirrup 40 defining an open eyelet 41 at the lower or trailing end thereof. This stirrup 40 has a size and shape for slide-fit reception into the lower, larger diameter segment of the femoral tunnel 18, as previously described. In addition, the stirrup 40 includes a pair of diametrically opposed and outwardly radiating external tabs 42 having a size and shape for sliding mated reception into the notches 34 formed at the lower end of the femoral tunnel 18.

An upper or leading end of the femoral stem 38 is pivotally connected to the anchor pin 26. As shown, this anchor pin 26 has a generally bullet-shaped profile to define a tapered nose 26' and a diametric size to fit slidably through the narrower upper segment of the femoral tunnel 18. A rear end of the anchor pin 26 is suitably slotted so that the anchor pin may be pivotally rotated to a position generally in-line with a central axis of the stirrup rod 38. In addition, the leading and trailing ends of the anchor pin 26 are desirably apertured as indicated by reference numerals 44 and 46 to accommodate pass-through reception of sutures leading and trailing sutures 48 and 50, respectively (FIG. 4). FIG. 5 illustrates pivoting motion of the anchor pin 26 from an initial position oriented generally in-line with the stirrup rod 38, to an alternative or locked position oriented generally perpendicular to the stirrup rod 38.

The ligament graft 12 is looped through the enlarged stirrup 40 at the base end of the stirrup rod 38. The resultant trailing free ends of the ligament graft 12 are gathered and captured securely within a graft capture means 52 forming a portion of the tibial fixation unit 16. This graft capture means 52 is shown best in one preferred form in FIGS. 6–9, and comprises a generally cylindrical capture ring 54 supported by a plurality of axially extending arms 56 from a threaded base nut 58 carried on the threaded adjustment bolt 30. The capture ring 54 preferably defines internally ramped or tapered grip surfaces 60 (shown best in FIG. 8) for matingly seating and locking against similarly profiled ramped or tapered grip surface 62 (shown best in FIG. 9) on a wedge-shaped bolt head 64 at the leading or upper end of the adjustment bot 30. For optimal gripping of the ligament graft 12, these grip surfaces 60, 62 may be stepped or textured.

The loose free ends of the ligament graft 12 are placed over the tapered grip surfaces 62 of the bolt head 64, and the capture ring 54 is rotatably advanced on the adjustment bolt 30 toward the bolt head 64 sufficient to bindingly engage and clamp the ends of the ligament graft 12 between the capture ring 54 and the bolt head 64. The capture ring 54 may be conveniently carried by the support arms 56 to permit rotation thereof relative to the associated threaded nut 58, thereby permitting the wedged grip surfaces 60 on the capture ring 54 to remain in substantial mating alignment with the associated grip surfaces 62 on the bolt head 64. A set or lock nut 66 is desirably provided to bear against the nut 58 of the graft capture means 52 to prevent back-rotation thereof subsequent to clamped engagement with the ligament graft 12. A specially designed cylinder wrench 67 (FIG. 4) is provided with a side-open slot 68 to accommodate placement of the wrench 67 over the adjustment bolt 30 for use in tightening the set nut 66. Importantly, the capture ring 54 has a diametric size and shape for slide-fit reception into the tibial tunnel 20, and includes a pair of diametrically opposed and outwardly radiating external tabs 70 for sliding mated reception into the notches 36 formed in the tibial tunnel 20.

The winged washer 28 is slidably mounted on the adjustment bolt 30 at a location below or trailing the graft capture means 52. As shown (FIGS. 4 and 6–7), the winged washer 28 comprises a central unthreaded sleeve member 72 having an elongated protruding nose segment, and a pair or outwardly radiating wings 74 to facilitate sliding axial advancement and retraction on the adjustment bolt 30. A second set or lock nut 76 is carried on the adjustment bolt 30 adjacent the winged washer 28 on the side opposite the graft capture means 52 and is positioned to be tightened against the recessed winged washer central sleeve member 72 by use of the slotted wrench 67. A re-usable screwdriver-type handle 78 is threadably mounted to a lower or outboard end of the elongated adjustment bolt 30 by means of an internal threaded nut 80 (FIG. 4).

The ligament graft 12 is assembled with the femoral and tibial components 14, 16 of the graft system 10 as described above, with the winged washer 28 positioned along the adjustment bolt 30 to provide a substantial space between the winged washer/lock nut 28, 76 and the graft capture means 52. The sutures 48, 50 on the anchor pin 26 are threaded upwardly through the tibial tunnel 20 and further through the femoral tunnel 18. The lead suture 48 at the nose end 26' of the anchor pin 26 is used to draw the anchor pin upwardly into the narrower upper segment of the femoral tunnel 18, with the result that the entire assembly is drawn upwardly and in a substantially in-line configuration into the proper position. Importantly, the outwardly radiating tabs 42 on the femoral stirrup 40 are drawn into registered engagement with the notches 34 formed in the larger lower segment of the femoral tunnel 18, whereas the outwardly radiating tabs 70 on the graft capture ring 54 are drawn into registered engagement with the notches 36 formed in the tibial tunnel 20. These tabs 42 and 70 on these components beneficially prevent post-operative rotation or other movements of the components relative to patient bone.

The anchor pin 26 is drawn upwardly to emerge from the upper end of the femoral tunnel 18, whereupon the anchor pin is rotated relative to the femoral stem 38 (as viewed in FIG. 1) to a position substantially perpendicular to the femoral stem. In this position, the anchor pin 26 provides a sturdy and relatively broad-based structure for engaging and seating against the relatively hard cortical bone surface surrounding the upper end of the femoral tunnel 18. The sutures 48, 50 provide a simple means for facilitated manipulation of the anchor pin 26, wherein these sutures 48, 50 are preferably monofilament for ease of subsequent removal and are further provided in different colors for ease of identification.

With the anchor pin 26 seated firmly against cortical patient bone, the handle 78 at the lower end of the assembled system components is manipulated to apply a suitable tension to the ligament graft 12. More particularly, the handle 78 is pulled downwardly to apply the desired tension force, whereupon the winged washer 28 is slidably advanced on the adjustment bolt 30 to a position with the wings 74 thereon seated firmly against the relatively hard cortical bone surface surrounding the lower end of the tibial tunnel 20. The winged washer 28 is rotatably adjusted on the rod 30 to seat the wings 74 in suitable recessed contours of the relatively hard cortical bone. When this position is achieved, the second set nut 76 is tightened against the winged washer 28 by use of the cylinder wrench 67. An anti-backout tab 82 (FIG. 6) in also provided on the sleeve member 72 of the winged washer 28 and may be bent to a position engaging the set nut 76 to affirmatively prevent component back-out axial movement of the winged washer 28 along the threaded bolt 30. The nose end of the winged washer sleeve member 72 also protrudes into the tibial tunnel 20 to provide a low profile device within the tibial tunnel. With the graft system 10 positioned as described, the handle 78 is threadably removed from the adjustment bolt 30, and the bolt 30 is trimmed or cut short as viewed in FIG. 1.

The ligament graft system 10 of the present invention is thus securely supported from the relatively hard cortical patient bone by the anchor pin 26 at the femoral end, and by the winged washer/set nut 28, 76 at the tibial end. Moreover, the set nut 76 permits the surgeon to closely select and adjust the specific tension applied to the ligament graft 12. The ligament graft is supported in a substantially centered position within the femoral and tibial bone tunnels, and in a manner which substantially precludes springing, twisting or side-to-side sway motion.

FIGS. 11 and 12 show alternative configurations for the tibial fixation unit, to include alternative means for capturing and retaining the free ends of the ligament graft 12. In this regard, FIG. 11 illustrates a modified capture cylinder means 152 in the form of an outer capture cylinder 154 having a part-cylindrical bore 90 formed therethrough to define an axially extending flat 92 at one side thereof lined by serrations 94. The adjustment bolt 30 carries a part-cylindrical bolt head 164 having a size and shape for substantially mated and slide-fit reception into the bore 90, and further to include serrations 96 for mating engagement with the serrations 94 within said bore 90. The free ends of the ligament graft 12 are placed into the capture cylinder bore 90 sufficiently to overlie and engage the serrations 94 therein, followed by slide-fit reception of the bolt head 164 into the bore 90. A set screw 98 is then fastened through a threaded port 100 formed in the capture cylinder 154 to seat within a detent 102 formed in the bolt head 164, to lock the bolt head 164 within the capture cylinder bore 90 with the bolt head serrations 96 clamped firmly against the capture cylinder serrations 94 to lock the ligament graft 12 tightly in place.

FIG. 12 shows a wedge-shaped bolt head 264 carried rotatably at the distal end of the adjustment bolt 30 and defining a pair of ramped or tapered clamp surfaces 262 on opposite sides thereof. These clamp surfaces 262 desirably include surface steps or serrations or other suitable surface texture. This bolt head 264 is shaped for mating fit into a generally V-shaped graft capture wedge 254 having a central threaded port 104 formed at the apex thereof for threaded reception of the adjustment bolt 30. The inboard faces of the graft capture wedge 254 define a pair of ramped or tapered clamp surfaces 260 for substantially mated engagement with the clamp surfaces 262 on the bolt head 264. At least one of the legs of the V-shaped capture wedge 254 has an opening 106 formed therein to receive the free ends of the graft ligament 12 (not shown in FIG. 12), whereupon the graft capture wedge 254 is advanced on the adjustment bolt 30 for tightly retaining the graft ligament 12 between the clamp surfaces 260 and 262.

Another alternative tibial fixation unit 316 is shown in FIGS. 13–16, in accordance with another alternative preferred embodiment of the invention. In this configuration, a modified adjustment rod 330 has an unthreaded construction to include a wedge-shaped bolt head 364 which may include surface serrations, as previously described. The adjustment rod 330 extends downwardly from the bolt head 364 and includes an initial smooth-surfaced segment 110 including a plurality of shallow annular grooves 112 formed therein as spaced positions along the length thereof, and an elongated lock segment defined by a series of enlarged surface elements or lands 114 shown in the form of a succession of generally hemispherically shaped lands. A graft capture ring 354 is carried adjacent the bolt head 364 by arms 356 joined to a base nut 358 slidably carried on the bolt segment 110.

The lower free ends of a ligament graft 12 are fitted over the bolt head 364, and then locked in place on the tibial fixation unit 316 by advancing the graft capture ring 354 into clamped engagement therewith in the same manner as previously described herein with respect to FIGS. 1–10. The base nut 358 is slidably advanced on the smooth-surfaced bolt segment 110 to advance the capture ring 354 into clamped engagement with the bolt head 364. In the desired clamped position, a lock ring 116 (shown in exaggerated size in FIG. 13) is fitted into an appropriate one of the grooves 112 at lower end of the base nut 358 to prevent back-movement relative to the bolt 330 and potential loosening of the graft 12.

With the ligament graft 12 assembled with the modified tibial fixation unit 316, and also with a femoral fixation unit such as the unit 14 shown and described in FIGS. 1–10, the femoral and tibial fixation units are threaded into the appropriate positions within the femoral and tibial bone tunnels, again as previously described. A suitable tensioning tool 118 (FIG. 16) is used to grasp the lower exposed end of the adjustment bolt 330, and to pull downwardly thereon to apply a selected tension to the ligament graft. In this regard, the tool 118 may include a nose 120 for pressing against patient bone (FIG. 16) to permit precision control over the applied tension. When the desired tension level is obtained, a lock clip 376 (FIGS. 14–16) is mounted onto the lower or free end of the adjustment bolt 330 to lock the bolt in place by firmly engaging cortical patient bone surrounding the lower end of the tibial bone tunnel.

The lock clip 376 has a generally wing-shaped configuration to include a central port 122 formed therein. This central port 122 is laterally open to permit reception of the shank of the adjustment bolt 330 therein, prior to disengaging the tensioning tool 118 from the bolt. Enlarged wings at the opposed sides of the lock clip 376 are sized and shaped to overlie and engage the cortical patient bone, with pointed teeth 124 being provided to seat with the bone and prevent lock clip rotation with respect thereto. Importantly, an upper or nose side of the lock clip 376 includes a shaped cavity 126 (FIG. 15) for firm, substantially snap-fit reception of a selected one of the hemispherically shaped lands 114, thereby securely locking the clip onto the bolt 330. As shown best in FIG. 15, this cavity 126 essentially comprises a tapered nose structure for partial reception into the lower end of the tibial bone tunnel, when the lock clip 376 is installed onto the adjustment bolt. A Morse taper pin 128 or the like can be seated within a laterally enlarged portion of the central port 122 to assist in retaining the lock clip in place. After installation of the lock dip 376, the tensioning tool 118 can be removed and the excess length of the adjustment bolt can be cut off, as previously described.

A variety of further modifications and improvements in and to the improved ligament graft system and related method of the present invention will be apparent to those persons skilled in the art. Accordingly, no limitation on the invention is intended by way of the foregoing description and accompanying drawings.

What is claimed is:

1. A ligament graft system for securely anchoring a ligament graft to first and second patient bones, said ligament graft system comprising:

a first fixation unit including an elongated stem having leading and trailing ends, an anchor pin pivotally mounted to said stem generally at said leading end thereof for movement between a first position disposed generally in-line with said stem and a second position disposed generally perpendicular to said stem, and a stirrup disposed generally at said trailing end of said stem and defining an open eyelet for looped reception of a ligament graft therethrough; and a second fixation unit including an elongated adjustment member having leading and trailing ends, graft capture means carried by said adjustment member generally at said leading end thereof for securely capturing the free ends of the ligament graft looped through said stirrup eyelet, and tension adjustment means carried generally at said trailing end of said adjustment member for adjustably selecting the tension applied to the ligament graft;

said first and second fixation units having a size and shape for sliding placement respectively into a pair of generally aligned bone tunnels formed in the first and second patient bones, with the ligament graft captured and extending therebetween, said anchor pin being adapted to emerge from the bone tunnel formed in the first patient bone for pivoting movement from said first position to said second position and to overlie and securely seat against a cortical bone surface, and said tension adjustment means being adjustably positioned along the length of said adjustment member for variably selecting the tension applied to the ligament graft and adapted to overlie and securely seat against a cortical bone surface at one end of the bone tunnel formed in the second patient bone;

said first fixation unit further includes suture means connected to said anchor pin for facilitated slide-fit drawing of said first fixation unit into the bone tunnel formed in the first patient bone; and said anchor pin in said first position having leading and trailing ends, and further wherein said suture means comprises a pair of sutures connected respectively to said leading and trailing ends of said anchor pin, said pair of sutures further facilitating pivotal movement of said anchor pin from said first position to said second position upon emergence from the bone tunnel formed in the first patient bone.

2. The ligament graft system of claim 1 wherein said first and second patient bones comprise the femur and tibia, said first fixation unit comprising a femoral fixation unit, and said second fixation unit comprising a tibial fixation unit.

3. The ligament graft system of claim 1 wherein said pair of sutures are removably connected to said anchor pin.

4. The ligament graft system of claim 1 wherein said pair of sutures are provided in different colors.

5. The ligament graft system of claim 1 wherein said first fixation unit further comprises at least one radially outwardly protruding antirotation tab for slide fit reception into a matingly shaped notch formed within the bone tunnel in the first patient bone.

6. The ligament graft system of claim 1 wherein said graft capture means of said second fixation unit comprises a bolt head and a capture cylinder for clamped engagement of the free ends of the ligament graft therebetween.

7. The ligament graft system of claim 6 wherein said bolt head has a generally wedge shape.

8. The ligament graft system of claim 6 wherein at least one of said bolt head and said capture cylinder define a serrated surface for gripping engagement with the ligament graft.

9. The ligament graft system of claim 6 wherein said adjustment member comprises an elongated bolt having a series of axially spaced lands formed thereon, and further wherein said tension adjustment means comprises a lock clip for secure attachment to said bolt at a selected position along the length thereof and in engagement with at least one of said lands, said lock clip having a size and shape for relatively low profile seated reception against a cortical bone surface at one end of the bone tunnel formed in the second patient bone.

10. The ligament graft system of claim 9 further including means for retaining said lock clip on said bolt.

11. The ligament graft system of claim 1 wherein said second fixation unit further comprises at least one radially outwardly protruding antirotation tab for slide fit reception into a matingly shaped notch formed within the bone tunnel in the second patient bone.

12. The ligament graft system of claim 1 further including tool means for removable connection to said second fixation unit for applying tension to the ligament graft during adjustable positioning of said tension adjustment means.

13. A ligament graft system for securely anchoring a ligament graft to first and second patient bones, said ligament graft system comprising:

a first fixation unit including an elongated stem having leading and trailing ends, an anchor pin pivotally mounted to said stem generally at said leading end thereof for movement between a first position disposed generally in-line with said stem and a second position disposed generally perpendicular to said stem, and a stirrup disposed generally at said trailing end of said stem and defining an open eyelet for looped reception of a ligament graft therethrough; and a second fixation unit including an elongated adjustment member having leading and trailing ends, graft capture means carried by said adjustment member generally at said leading end thereof for securely capturing the free ends of the ligament graft looped through said stirrup eyelet, and tension adjustment means carried generally at said trailing end of said adjustment member for adjustably selecting the tension applied to the ligament graft;

said first and second fixation units having a size and shape for sliding placement respectively into a pair of generally aligned bone tunnels formed in the first and second patient bones, with the ligament graft captured and extending therebetween, said anchor pin being adapted to emerge from the bone tunnel formed in the first patient bone for pivoting movement from said first position to said second position and to overlie and securely seat against a cortical bone surface, and said tension adjustment means being adjustably positioned along the length of said adjustment member for variably selecting the tension applied to the ligament graft and adapted to overlie and securely seat against a cortical bone surface at one end of the bone tunnel formed in the second patient bone;

said graft capture means of said second fixation unit comprising a bolt head and a capture cylinder for clamped engagement of the free ends of the ligament graft therebetween; and wherein said adjustment member comprises an elongated threaded bolt, and further wherein said tension adjustment means comprises a relatively low profile wing nut carried on said threaded bolt for relatively low profile seated reception against a cortical bone surface at one end of the bone tunnel formed in the second patient bone, and means for preventing movement of said wing nut along said bolt in a direction to reduce ligament graft tension.

14. A ligament graft placement method for securely anchoring a ligament graft to first and second patient bones, said ligament graft placement method comprising the steps of:

forming first and second generally aligned bone tunnels respectively in the first and second patient bones;

providing a first fixation unit having an elongated stem with leading and trailing ends, anchor means carried by said stem generally at said leading end thereof, and graft connection means disposed generally at said trailing end of said stem for connection with a ligament graft;

providing a second fixation unit including an elongated bolt having leading and trailing ends, graft capture means carried by said bolt generally at said leading end thereof for securely capturing a ligament graft, and tension adjustment means carried generally at said trailing end of said bolt for adjustably selecting the tension applied to the ligament graft;

connecting a ligament graft at one end to the graft connection means of the first fixation unit, and at an opposite end to the graft capture means of the second fixation unit;

slidably fitting a leading end of the first fixation unit through the second bone tunnel and further into the first bone tunnel, with the ligament graft connected to the first and second fixation units, for placing the first fixation unit within the first bone tunnel and for placing the second fixation unit within the second bone tunnel;

adjustably positioning the anchor means at the leading end of the first fixation unit to emerge from the first bone tunnel and to overlie and seat against a cortical bone surface adjacent the first bone tunnel;

pulling the second fixation unit to apply a selected tension to the ligament graft connected between the first and second fixation units; and adjustably positioning the tension adjustment means to engage and securely seat against a cortical bone surface adjacent one end of the second bone tunnel to maintain the selected ligament graft tension.

15. The ligament graft placement method of claim 14 wherein the first and second patient bones comprise the femur and tibia, and further wherein the first fixation unit comprises a femoral fixation unit, and the second fixation unit comprises a tibial fixation unit.

16. The ligament graft placement method of claim 14 further including the step of attaching at least one suture to the anchor means for facilitated slide-fit drawing of the first fixation unit into the first tunnel, and for facilitated manipulation of the anchor means to seat against the cortical bone surface.

17. The ligament graft placement method of claim 14 wherein the anchor means comprises an anchor pin mounted on said stem for pivoting movement between a first position generally in-line with said stem and a second position generally perpendicular to said stem, said step of adjustably positioning the anchor means comprising pivoting said anchor pin from said first position to said second position upon emergence from said first bone tunnel.

18. The ligament graft placement of claim 17 further including the step of attaching a pair of sutures to opposite ends of the anchor pin, and wherein said step of adjustably positioning the anchor means comprises manipulating said sutures to pivot said anchor pin from said first position to said second position.

19. The ligament graft placement method of claim 18 wherein said pair of sutures are provided in different colors.

20. The ligament graft placement method of claim 14 further including the step of forming at least one radially outwardly extending notch along the first bone tunnel, and further including the step of providing at least one radially outward protruding antirotation tab on the first fixation unit for substantially mated slide fit reception into the bone tunnel notch.

21. The ligament graft placement method of claim 14 further including the step of forming at least one radially outwardly extending notch along the second bone tunnel, and further including the step of providing at least one radially outward protruding antirotation tab on the second fixation unit for substantially mated slide fit reception into the bone tunnel notch.

* * * * *